(12) United States Patent
Parkins

(10) Patent No.: US 8,638,963 B2
(45) Date of Patent: Jan. 28, 2014

(54) EAR DEFENDER WITH CONCHA SIMULATOR

(75) Inventor: John W. Parkins, Ithaca, NY (US)

(73) Assignee: Red Tail Hawk Corporation, Ithaca, NY (US)

( * ) Notice: Subject to any disclaimer, the term of this patent is extended or adjusted under 35 U.S.C. 154(b) by 450 days.

(21) Appl. No.: 12/789,942

(22) Filed: May 28, 2010

(65) Prior Publication Data

US 2010/0303270 A1 Dec. 2, 2010

Related U.S. Application Data

(60) Provisional application No. 61/182,921, filed on Jun. 1, 2009.

(51) Int. Cl.
| | | |
|---|---|---|
| *H04R 25/00* | (2006.01) | |
| *H04R 5/02* | (2006.01) | |
| *A61F 11/06* | (2006.01) | |
| *G10K 11/16* | (2006.01) | |

(52) U.S. Cl.
USPC ............ 381/322; 181/129; 381/71.6; 381/72; 381/151; 381/309; 381/370; 381/371; 381/372

(58) Field of Classification Search
USPC ............................ 381/322, 151, 370, 71.6, 72
See application file for complete search history.

(56) References Cited

U.S. PATENT DOCUMENTS

| | | | | |
|---|---|---|---|---|
| 2,643,729 A | * | 6/1953 | McCracken | 181/242 |
| 2,946,862 A | * | 7/1960 | Wadsworth et al. | 381/72 |
| 3,683,130 A | * | 8/1972 | Leonard | 455/575.2 |
| 3,952,158 A | * | 4/1976 | Kyle et al. | 381/72 |
| 4,006,318 A | * | 2/1977 | Sebesta et al. | 381/151 |
| 4,037,064 A | * | 7/1977 | Yasuda | 381/26 |
| 4,088,849 A | * | 5/1978 | Usami et al. | 379/430 |
| 4,441,576 A | * | 4/1984 | Allen | 181/129 |
| 4,924,502 A | * | 5/1990 | Allen et al. | 381/72 |
| 4,972,491 A | * | 11/1990 | Wilcox, Jr. | 381/375 |
| 5,305,387 A | * | 4/1994 | Sapiejewski | 381/71.6 |
| 5,333,206 A | * | 7/1994 | Koss | 381/370 |
| 5,357,585 A | * | 10/1994 | Kumar | 381/373 |
| 5,426,719 A | * | 6/1995 | Franks et al. | 704/228 |
| 5,551,090 A | * | 9/1996 | Thompson | 2/209 |
| 5,887,286 A | * | 3/1999 | Waldron | 2/209 |

(Continued)

FOREIGN PATENT DOCUMENTS

WO 2006118516 A1 11/2006

OTHER PUBLICATIONS

Type 3.4 (artificial ear) Pinna simulator—simplified. International Telecommunications Union standard ITU-T P.57. Nov. 2005.

(Continued)

*Primary Examiner* — David Warren
*Assistant Examiner* — Christina Russell
(74) *Attorney, Agent, or Firm* — Brown & Michaels, PC

(57) ABSTRACT

A hearing protection system with talk-through having a pair of rigid earcups enclosing a microphone, amplifier and speaker. A concha simulator, having a volume simulating that of the concha of a human ear, is acoustically coupled to the microphone, and also to the outside through an opening in the earcup. By coupling the microphone to the concha simulator, instead of directly to the outside, the acoustic response of the talk-through more accurately represents the hearing of a user.

10 Claims, 3 Drawing Sheets

(56) References Cited

U.S. PATENT DOCUMENTS

| | | | |
|---|---|---|---|
| 6,118,878 A * | 9/2000 | Jones | 381/72 |
| 6,445,805 B1 * | 9/2002 | Grugel | 381/330 |
| 6,567,525 B1 * | 5/2003 | Sapiejewski | 381/71.6 |
| 6,683,965 B1 * | 1/2004 | Sapiejewski | 381/380 |
| 7,212,645 B2 * | 5/2007 | Le Gette et al. | 381/370 |
| 7,352,871 B1 * | 4/2008 | Mozo | 381/72 |
| 7,564,989 B2 * | 7/2009 | Schanz | 381/328 |
| 8,059,851 B2 * | 11/2011 | Pfanner | 381/379 |
| 8,213,643 B2 * | 7/2012 | Hemer | 381/151 |
| 8,224,011 B2 * | 7/2012 | Heringslack | 381/355 |
| 2003/0095670 A1 * | 5/2003 | Wurtz | 381/71.6 |
| 2003/0185403 A1 * | 10/2003 | Sibbald | 381/71.6 |
| 2004/0165742 A1 * | 8/2004 | Shennib et al. | 381/326 |
| 2006/0013409 A1 * | 1/2006 | Desloge | 381/72 |
| 2006/0153414 A1 * | 7/2006 | Liao | 381/371 |
| 2008/0025524 A1 * | 1/2008 | Vaudrey et al. | 381/72 |
| 2009/0041285 A1 * | 2/2009 | Parkins et al. | 381/372 |
| 2010/0080400 A1 * | 4/2010 | Sibbald et al. | 381/71.6 |
| 2011/0164757 A1 * | 7/2011 | Sibbald et al. | 381/58 |
| 2011/0261965 A1 * | 10/2011 | Parkins | 381/1 |

OTHER PUBLICATIONS

Hammershoi et al. "Sound transmission to and within the human ear canal" J. Acoust. Soc. Am. 100(1). Jul. 1996.

Burkhard et al. "Anthropometric Manikin for Acoustic Research." J. Acoust. Soc. Am. 58(1). Jul. 1975.

* cited by examiner ial Application No. 61/182,921, filed
EAR DEFENDER WITH CONCHA SIMULATOR

REFERENCE TO RELATED APPLICATIONS

This application claims one or more inventions which were disclosed in Provisional Application No. 61/182,921, filed Jun. 1, 2009, entitled "Talk-Through Listening Device Channel Switching". The benefit under 35 USC §119(e) of the U.S. provisional application is hereby claimed, and the aforementioned application is hereby incorporated herein by reference.

ACKNOWLEDGMENT OF GOVERNMENT SUPPORT

This invention was made with Government support under SBIR Phase II contract N68335-06-C-0372, awarded by the US Navy. The government has certain rights in the invention.

BACKGROUND OF THE INVENTION

1. Field of the Invention

The invention pertains to the field of hearing protection. More particularly, the invention pertains to hearing protection using an artificial ear structure.

2. Description of Related Art

FIG. 1 shows a hearing protection system with talk-through, in the form of a headset 13 worn by a user 14. The headset has a right earcup 1 and a left earcup 2, which serve to reduce the ambient noise level heard by the user 14. Such protection systems are typically used in high-noise environments such as aircraft carrier decks, factories, etc. In order that the user 14 retain some ability to hear what is going on around him, microphones 3 and 4 feed a reduced amount of external sound to the user 14 through amplifiers 5 and 6, which power audio transducers 7 and 8. The amplifiers 5 and 6 can include various features known to the art, such as filtering, volume limiting or equalizing, etc. The audio transducers can be speakers or piezoelectric or magnetic transducers in earplugs (wired or wireless), as is known to the art.

FIG. 2 shows a talk-through earcup of the prior art in more detail, with FIG. 6 showing a section of the earcup along the lines 6-6 of FIG. 2. The point here is that typical prior art talk-through systems use a microphone 23 coupled to the outside of an earcup 21 through a hole or tube 20. The microphone 23 is sealed in a small chamber 24 so that the sound doesn't get into the earcup 21 volume. A resilient pad 22 seals the earcup around the pinna of a user's ear, as is common in most around-the-ear type earphones.

"Artificial ears" are used as objective measuring apparatus to measure sound levels, as for example for frequency response, sensitivity and distortion measurements on earphones. They enable electroacoustical measurements on either insert earphones or headphones to be carried out under well-defined acoustical conditions, which are of great importance for the comparability of different designs and the reproducibility of measurements.

International Telecommunications Union standard ITU-T P.57 (November 2005) defines a standard for artificial ears. The geometry of Type 3.4 artificial ears ("Pinna simulator—simplified") is shown in FIG. 8/P.57 of the standard (page 16).

Studies, such as "Sound transmission to and within the human ear canal", Hammershøi and Møller, J. Acoust. Soc. Am. 100 (1) (July 1996), have shown that recordings using a microphone in a blocked human ear canal retain the acoustic timing cues and directional dependence needed for accurate localization. The concha geometry is needed to simulate human ear response, regarding localization, while the ear canal geometry is not. The blocked canal recordings are frequency equalized when played back for the user to compensate for the ear canal, speaker, microphone, amplifier, and other responses to provide the proper frequency response at the user's ear canal.

SUMMARY OF THE INVENTION

The invention provides an improved hearing protection system with talk-through using earcups which have microphones, amplifiers and speakers, utilizing a structure based on a modified artificial ear.

BRIEF DESCRIPTION OF THE DRAWING

FIG. 1 shows a diagram of a hearing protection system with talk-through.

FIG. 2 shows a side view of a prior art earcup with talk-through.

DETAILED DESCRIPTION OF THE INVENTION

Figure 1:
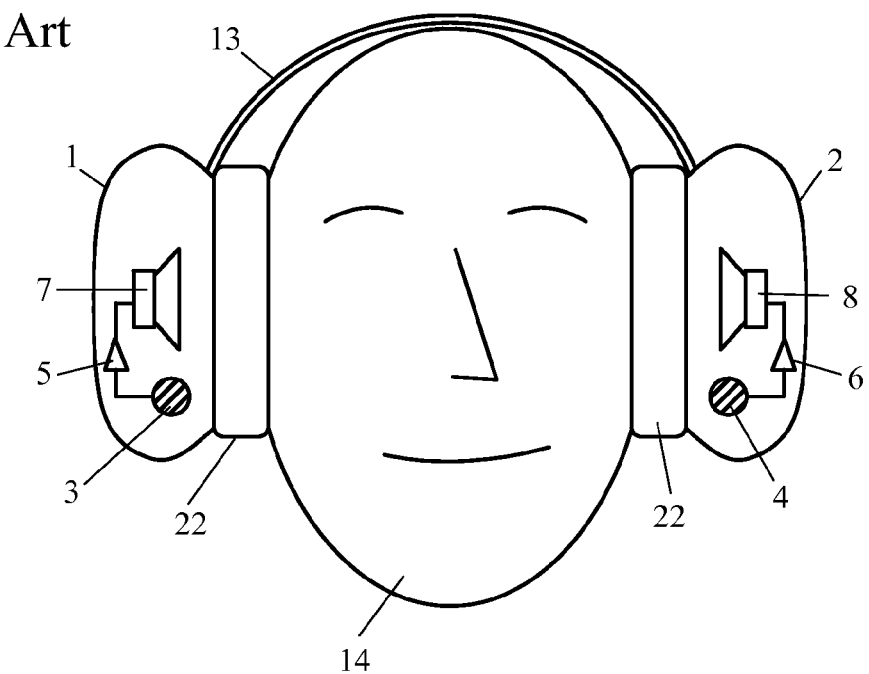
Figure 5:
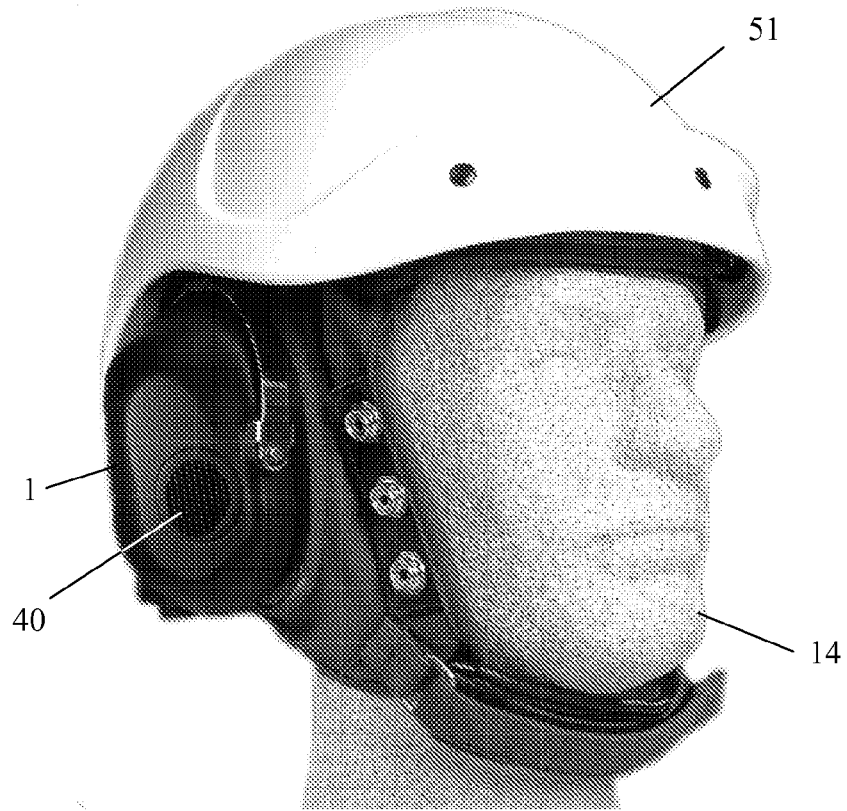
FIG. 5 shows a hearing protection system worn under a helmet.
Figure 4:
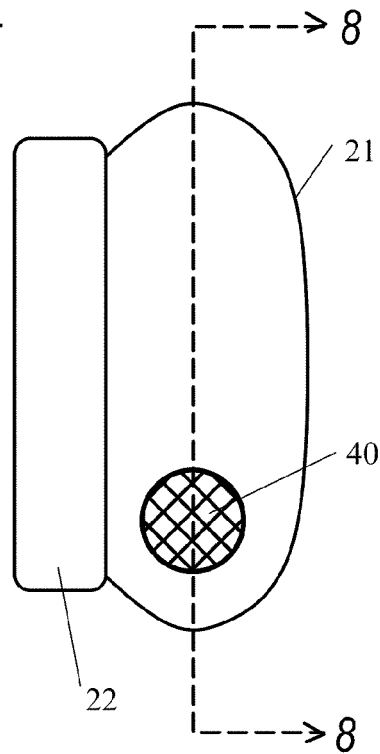
FIG. 4 shows a side view of an earcup incorporating the invention in a second embodiment.

FIG. 5 depicts a talk-through system incorporating a helmet 51 and earcups (right earcup 1 is visible in FIG. 5, left earcup 2 being on the other side of the user's head), as shown in diagrammatic form in FIG. 1.The helmet-based talk-through system can be used in conjunction with wired or wireless communications earplugs. The earcups 1 and 2 block ambient sounds while the microphones 3 and 4 and speakers 7 and 8 and amplifiers 5 and 6 restore those sounds at safe levels. The rigid earcup shell is designed to generally minimize acoustic transmission to the inside of the earcup. The speakers 7 and 8 can be in the earcups 1 and 2, or in earplug (wired or wireless) worn inside the earcups. Earplugs are used with earcups when double hearing protection is needed such as in loud environments. The screen 40 (and concha simulator underneath) are preferable located where the human concha is located, underneath the earcup 1, to provide the best response. However, other concha simulator locations on the earcup, such as forward-facing as indicated in FIG. 4 are acceptable.

The earcups 1 and 2 incorporate a significantly modified version of the artificial ears described in the International Telecommunications Union standard ITU-T P.57 (November 2005), in the form of a concha simulator having a volume similar to that of a human ear. By coupling the microphone to the concha simulator, instead of directly to the outside, the acoustic response of the talk-through more accurately reproduces the directional hearing characteristics of a user, making environmental clues fed to the user through the talk-through system more useful.

An article by Burkhard and Sachs in the Journal of Acoustical Society of America ("Anthropometric manikin for acoustic research", *J. Acoust. Soc. Am.*, Vol. 58, No. 1 July 1975) states that average concha volume is 4.65 cc for men and 3.94 cc for women with standard deviation of 0.76 cc for men and 0.81 cc for women. Hence, the concha simulator of the invention is preferably approximately 4.30 cc in volume. However, adding 2 standard deviations for women and 2 for men gives a possible volume range for the concha simulator of approximately 6.17 cc to 2.32 cc. The average depth of the human concha is approximately 1.29 cm, while the average concha breadth is 1.80 cm, according to Burkhard and Sachs. The concha simulator should preferably be approximately this deep as well with a similar breadth. The overall concha simulator length should be approximately 1.85 cm, which is determined by dividing the concha volume by the concha depth and length. However, various other reasonable geometries can be used. The concha simulator should be rigid and not allow sound to penetrate into the earcup, else the user will be exposed to noise.

As shown in FIG. 5, screen 40 has been mounted over the concha region of the artificial ear to protect a microphone mounted within from debris and fluids and also acts to dampen the acoustic response. This screen is not used in the ITU artificial ear. The screen 50 can be made of metal mesh, textile, a gas-permeable membrane or other material that protects the microphone from debris, fluids, rain, snow, and other detrimental materials to microphones. Acoustic damping material, such as foam, can also be used in the concha bowel of the artificial ear to dampen the acoustic response.

Figure 3:
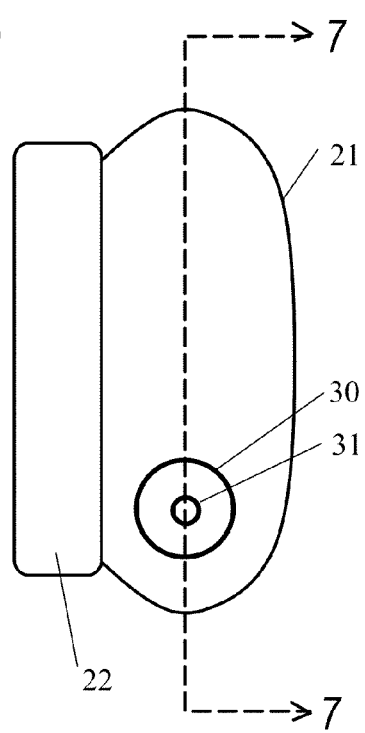
FIG. 3 shows a side view of an earcup incorporating the invention in a first embodiment.
Figure 6:
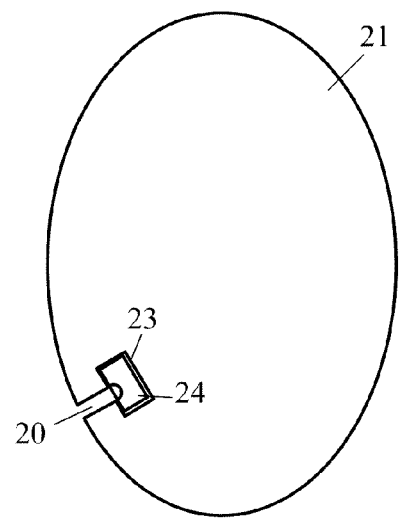
FIG. 6 shows a sectional view along the lines 6-6 of the earcup of FIG. 2.
Figure 7:
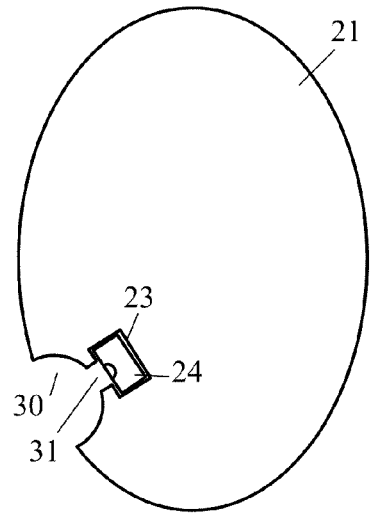
FIG. 7 shows a sectional view along the lines 7-7 of the earcup of FIG. 3.

FIG. 3 shows a basic embodiment of the invention, with FIG. 7 being a sectional view along lines 7-7 in FIG. 3. It will be understood that the amplifier and transducer details are omitted from FIGS. 7-9, as such details are not necessary to an understanding of the invention, and can be any design as known to the art.

Figure 2:
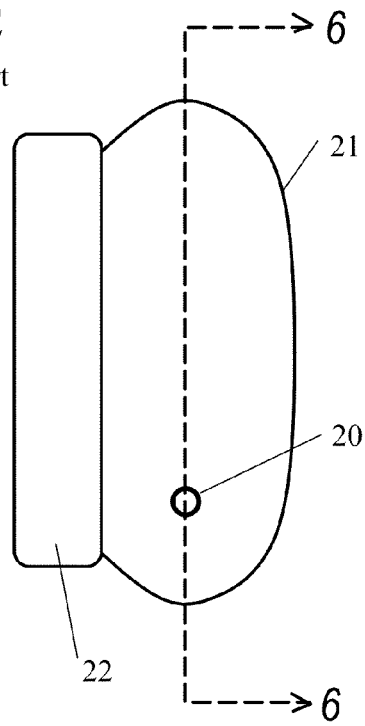

The opening is no longer a small hole, as shown at 20 in prior art FIG. 2, but a large opening 30 with an associated volume. This volume 30 forms the concha simulator, and, as discussed above, is preferably between 6.17 cc to 2.32 cc to simulate the general size of a human concha. The microphone 23 is sealed in a small chamber 24 and directed through an opening 31 into the volume 30 so that it measures the sound pressure level (SPL) in the volume 30.

Figure 8:
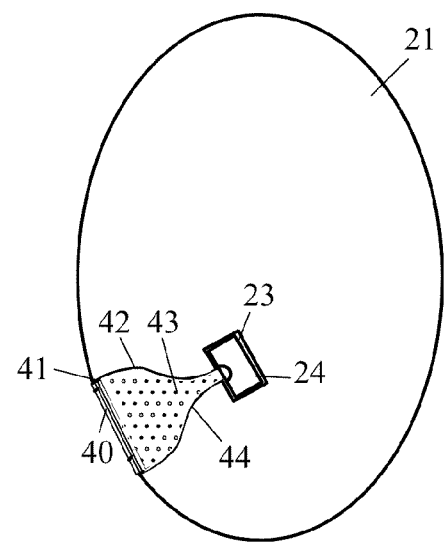
FIG. 8 shows a sectional view along the lines 8-8 of the earcup of FIG. 4.

FIG. 4 shows another embodiment of the invention, with FIG. 8 being a sectional view along lines 8-8 of FIG. 4. The embodiment shown in these FIGS. 4 and 8 builds on the embodiment of FIGS. 3 and 7. There is a screen 40 on the outside of the concha simulator 42 to protect a gas-permeable membrane 41, located directly behind it. The screen 40 keeps objects and fingers from poking a hole through the membrane 41. The screen 40 can be made of metal mesh, plastic mesh or slots or other materials. The membrane 41 can be made of expanded PTFE material, PET-nonwoven material, polyester, cellulose, nylon or cloth, or other materials that are gas-permeable but help to keep out dust, debris, and/or liquid. The material used should not affect the acoustic response appreciably or else substantial electrical equalization is needed.

Acoustic foam 43 is preferably placed in the volume of the concha simulator 42 to dampen acoustic resonances. The microphone 23 is sealed in a small chamber 24, but is coupled to the concha simulator 42 using a horn-shaped tube 44. The horn-shaped tube 44 can be used to acoustically amplify sounds above 1 kHz if desired, with the length and cross-sectional area of the tubing and flaring of the horn determining the acoustic amplification. The relationship between a length of straight tubing and resonance with a microphone mounted at the end is approximately wavelength $=34,300/(4\times$ frequency). For example, using a straight tube of length 1.72 cm will boost the frequency response at approximately 5,000 Hz. The relationship between a length of horn-shaped tubing and amplification frequency is more complicated, but can be found in many acoustics books.

It is advantageous to use a relatively soft material for the tubing so that the microphone is vibration isolated from the rigid earcup. However, the tubing must be stiff enough that sound doesn't propagate through the walls of the tubing and into the earcup volume.

Figure 9:
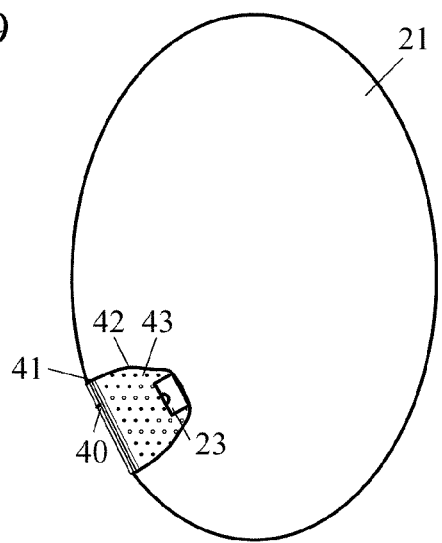
FIG. 9 shows a sectional view as in FIG. 8, with a variation in the position of the microphone.

Alternatively, as shown in FIG. 9, the microphone 23 could be mounted inside the concha simulator 42.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A hearing protection system with talk-through, comprising a pair of earcups, each earcup comprising:
    a) a rigid earcup shell;
    b) a concha simulator within the earcup shell, comprising a volume between 2.32 cc and 6.17 cc simulating a volume of a concha of a human ear, coupled to an opening in the rigid earcup shell;
    c) a microphone acoustically coupled to the concha simulator;
    d) an amplifier coupled to the microphone; and
    e) an audio transducer coupled to the amplifier to generate sound in a user's ear canal.

2. The hearing protection system of claim 1, in which the microphone is inside the concha simulator.

3. The hearing protection system of claim 1, in which the microphone is outside the concha simulator, acoustically coupled to the concha simulator through a tube.

4. The hearing protection system of claim 3, in which the tube is flexible.

5. The hearing protection system of claim 3, in which the tube is horn-shaped.

6. The hearing protection system of claim 1, further comprising a screen on an outside of the concha simulator, over the opening in the earcup shell.

7. The hearing protection system of claim 1, further comprising a gas-permeable membrane inside the opening of the earcup shell.

8. The hearing protection system of claim 7, in which the membrane is made of a material selected from a group consisting of expanded PTFE material, PET-nonwoven material, polyester, cellulose, nylon and cloth.

9. The hearing protection system of claim 1, in which the concha simulator contains acoustic foam.

10. The hearing protection system of claim 1, in which the volume of the concha simulator is approximately 4.30 cc.

* * * * *